(12) United States Patent
Al-Dhabi et al.

(10) Patent No.: US 10,036,048 B1
(45) Date of Patent: Jul. 31, 2018

(54) **PROCESS FOR OBTAINING A NAPHTHOQUINONE DERIVATIVE FROM *STREPTOMYCES* SP**

(71) Applicant: KING SAUD UNIVERSITY, Riyadh (SA)

(72) Inventors: Naif Abdullah Al-Dhabi, Riyadh (SA); Savarimuthu Ignacimuthu, Tamil Nadu (IN); Chandrasekar Balachandran, Tamil Nadu (IN); Veeramuthu Duraipandiyan, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/839,594

(22) Filed: Dec. 12, 2017

Related U.S. Application Data

(63) Continuation of application No. 15/719,405, filed on Sep. 28, 2017, now abandoned.

(51) Int. Cl.
| | | |
|---|---|---|
| *A61P 31/04* | (2006.01) | |
| *A61P 31/10* | (2006.01) | |
| *A61P 35/00* | (2006.01) | |
| *C07D 498/08* | (2006.01) | |
| *C12P 17/18* | (2006.01) | |

(52) U.S. Cl.
CPC ............ *C12P 17/188* (2013.01); *A61P 31/04* (2018.01); *A61P 31/10* (2018.01); *A61P 35/00* (2018.01); *C07D 498/08* (2013.01)

(58) Field of Classification Search
CPC ......... C12P 17/188; A61P 31/04; A61P 31/10; A61P 35/00; C07D 498/08
USPC ........................................................ 540/492
See application file for complete search history.

(56) References Cited

U.S. PATENT DOCUMENTS

2013/0095931 A1    2/2013  Imhoff et al.

OTHER PUBLICATIONS

Umezawa, K. et al., "Isolation from Streptomyces of a Novel Napthoquinone Compound, Naphthablin, That Inhibits Abl Oncogene Functions," *J. of Antibiotics*, 48:7, pp. 604-607 (1995).
Foreign patents and/or publications were properly filed in parent U.S. Appl. No. 15/719,405, filed Sep. 28, 2017, the priority of which is claimed.

*Primary Examiner* — Kristin A Vajda
(74) *Attorney, Agent, or Firm* — Richard C. Litman

(57) ABSTRACT

The process for obtaining a naphthoquinone derivative from *Streptomyces* sp. includes providing a seed inoculum of a strain of *Streptomyces* sp.; culturing the *Streptomyces* sp. in a culture nutrient medium; centrifuging the culture nutrient medium to provide a supernatant and a biomass precipitate; admixing a water immiscible solvent to the supernatant to produce a water immiscible solvent extract layer and a water layer; and isolating the antimicrobial and cytotoxic compound from the water immiscible solvent extract layer by performing silica gel chromatography. The naphthoquinone derivative has the following chemical structure:

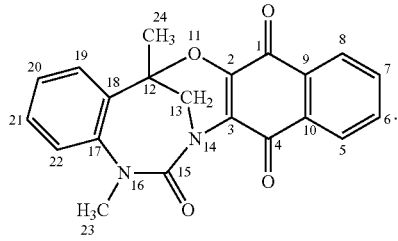

11 Claims, 11 Drawing Sheets

PROCESS FOR OBTAINING A NAPHTHOQUINONE DERIVATIVE FROM *STREPTOMYCES* SP

CROSS-REFERENCE TO RELATED APPLICATIONS

This application is a continuation of Ser. No. 15/719,405, filed Sep. 28, 2017, now pending.

BACKGROUND OF THE INVENTION

1. Field of the Invention

The present invention relates to microbial extracts, and particularly to *Streptomyces* sp. extracts having antimicrobial and cytotoxic (anti-cancer) properties.

2. Description of the Related Art

Microorganisms have proven to be an excellent source of novel natural products. For example, in the microbial community, *Bacillus* sp., *Pseudomonas* sp., *Mycobacteria, Cyanobacteria* and *Actinomyces* frequently produce natural products of significance. *Bacillus* sp. and *Pseudomonas* sp. are usually found to produce peptides or modified peptides, phenazines, and aliphatic compounds. *Cyanobacteria* are found to produce toxic or non-toxic peptides and polyketides.

Microorganisms belonging to the genus *Actinomyces*, especially *Streptomyces* sp. are best known as prolific producers of economically important bioactive compounds that have found their application as antibiotics, herbicides, pesticides, anti-parasitics, as well as industrially useful enzymes such as cellulase and xylanase. *Actinomycetes* are producers of structurally diverse metabolites namely, β-lactum antibiotics, amoxicillin, thienamycin, macrolides, streptomycin and erythromycin; anthracyclines, daunorubicin, doxorubicin; polyketides, rapamycin, FK-506, peptide antibiotics, virginiamycin, pristinamycin; aminoglycosides, gentamicin, and kanamycin.

*Streptomyces*, a type of Gram positive filamentous bacteria, are widely distributed in a variety of natural and man-made environments. *Streptomyces* are known to be producers of many secondary metabolites having different biological activities, such as antibacterial, antifungal, anti-parasitic, antitumor, and immunosuppressive actions. They are not particularly pathogenic, although some species can also cause infections. Some have been shown to be potent inducers of inflammatory responses in vitro and in vivo. Secondary metabolites are potent antibiotics, which have made *Streptomyces* the primary antibiotic producing organisms exploited by the pharmaceutical industry. Around 23,000 bioactive secondary metabolites produced by microorganisms have been reported and over 10,000 of these compounds are produced by *Actinomycetes*, representing 45% of all bioactive microbial metabolites discovered. Among *Actinomycetes*, around 7,600 compounds are produced by the *Streptomyces* species.

Thus, a compound derived from *Streptomyces* sp. having therapeutic properties thereby solving the aforementioned problems is desired.

SUMMARY OF THE INVENTION

A purified naphthoquinone derivative obtained from *Streptomyces* sp. has the following chemical structure:

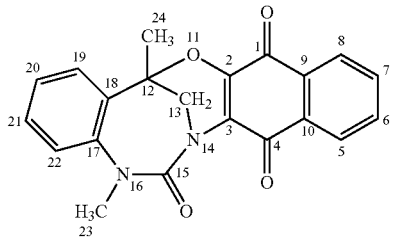 [SMILES: CN1C(=O)N2CC(C)(OC3=C2C(=O)c2ccccc2C3=O)c2ccccc21]

A process for obtaining the naphthoquinone derivative comprises the steps of: providing a seed inoculum of a strain of *Streptomyces* sp.; culturing the *Streptomyces* sp. in a culture nutrient medium at a temperature ranging from about 25° C. to about 30° C. for about 10 to 15 days; centrifuging the culture nutrient medium at about 8000 g for about 20 min to provide a supernatant and a biomass precipitate; admixing a water immiscible solvent to the supernatant in a ratio of 1:1 to produce a water immiscible solvent extract layer and a water layer; and isolating the naphthoquinone derivative from the water immiscible solvent extract layer.

These and other features of the present invention will become readily apparent upon further review of the following specification.

DETAILED DESCRIPTION OF THE PREFERRED EMBODIMENTS

Figure 1:
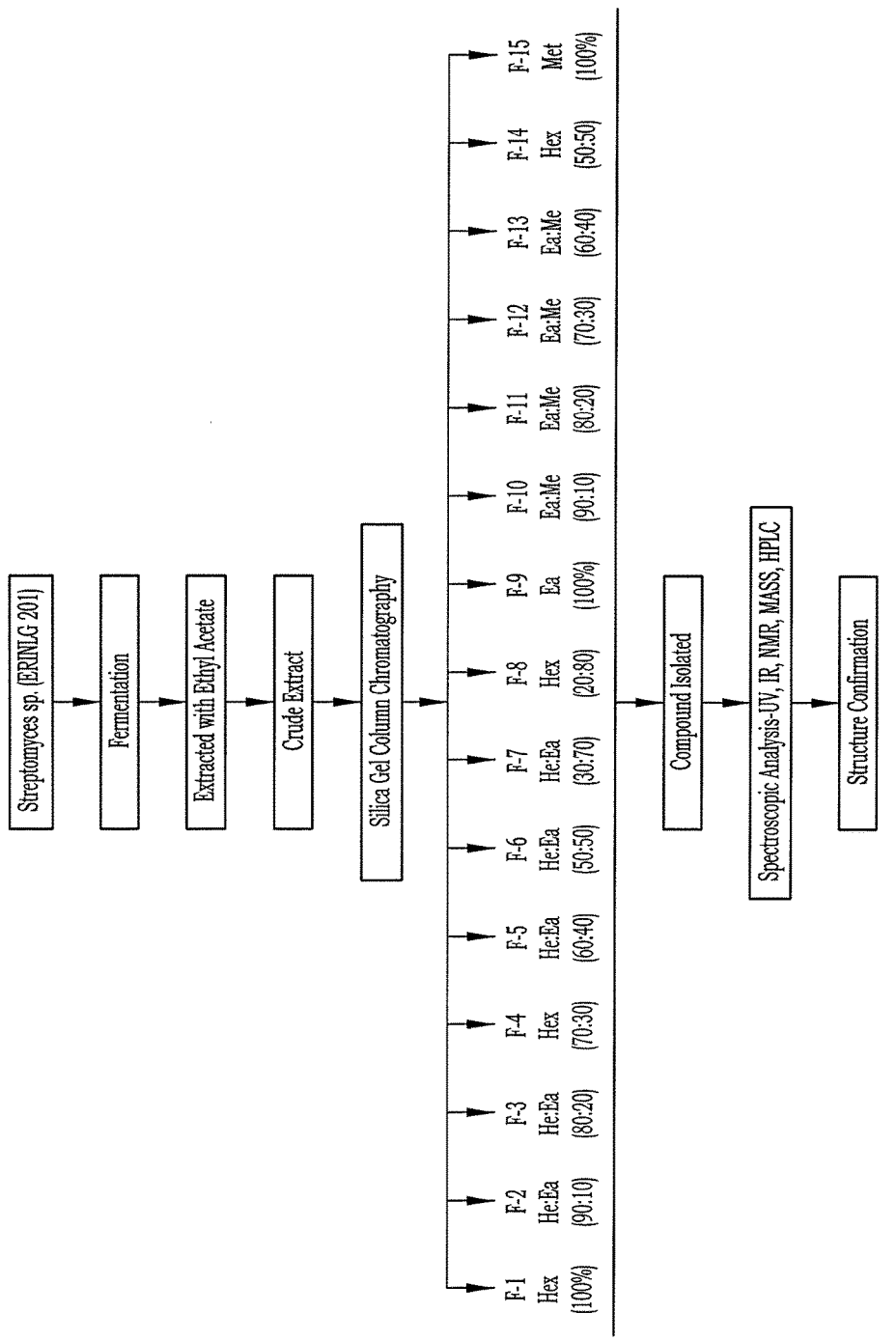
FIG. 1 shows a flow chart illustrating the process of isolating the naphthoquinone from *Streptomyces* sp.

A process for obtaining a naphthoquinone derivative from *Streptomyces* sp. includes providing a seed inoculum of a strain of *Streptomyces* sp.; culturing the *Streptomyces* sp. in a culture nutrient medium; centrifuging the culture nutrient medium to provide a supernatant and a biomass precipitate; admixing a water immiscible solvent to the supernatant in a ratio of 1:1 to produce a water immiscible solvent extract layer and a water layer; and isolating the antimicrobial and cytotoxic compound from the water immiscible solvent extract layer by performing silica gel chromatography. Preferably, the *Streptomyces* sp. is cultured in a culture nutrient medium at a temperature ranging from 25° C. to 30° C. for about 10 to 15 days. The culture nutrient medium can be centrifuged at about 8000 g for about 20 min. The naphthoquinone derivative has the following chemical structure:

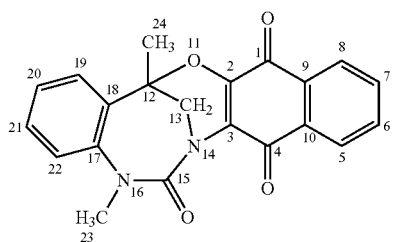 [SMILES: CN1C(=O)N2CC(C)(OC3=C2C(=O)c2ccccc2C3=O)c2ccccc21]

The water immiscible solvent can be ethyl acetate. The step of admixing a water immiscible solvent to the supernatant can be conducted at least two times and the water immiscible solvent extract layers can be combined to produce a water immiscible solvent extract from which the naphthoquinone derivative can be isolated. Isolating the naphthoquinone derivative from the water immiscible solvent extract can include drying the combined water immiscible solvent extract over anhydrous sodium sulphate; concentrating the water immiscible solvent fraction by evaporation to produce a concentrated volume of the water immiscible solvent fraction; and isolating the purified compound by performing silica gel chromatography. Performing silica gel chromatography can include loading the concentrated volume of the water immiscible solvent fraction on a silica gel column; eluting the silica gel column with a fractionating solvent; collecting solvent fractions at various time intervals; and isolating the active naphthoquinone derivative from at least one of the solvent fractions by evaporating the solvent under reduced pressure. The silica gel in the column can be of 100-200 mesh size. The fractionating solvent can include hexane, ethyl acetate, methanol or combinations thereof. Preferably, the fractionating solvent includes an ethyl acetate:methanol ratio of 70:30.

The naphthoquinone derivative, also referred to herein as "Bluemomycin," can be an active agent in a pharmaceutical composition including a pharmaceutically acceptable carrier. The pharmaceutical composition can include the naphthoquinone derivative and a pharmaceutically acceptable carrier. The pharmaceutical composition can be administered to a patient for treating microbial infections, e.g., microbial infections caused by gram positive bacteria, gram negative bacteria and/or fungi. The pharmaceutical composition can be administered to a patient for treating cancer, such as lung cancer.

Pharmaceutically acceptable carriers can be inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. Accordingly, the pharmaceutically acceptable carrier can include alcohol, dimethyl sulfoxide (DMSO), a physiological saline, a lipid based formulation, a liposomal formulation, a nanoparticle formulation, a micellar formulation, a water soluble formulation, a biodegradable polymer, an aqueous preparation, a hydrophobic preparation, a lipid based vehicle, or a polymer formulation.

A method of treating microbial infection can include administering to a patient in need thereof a therapeutically effective amount of the naphthoquinone derivative or a pharmaceutical composition including the naphthoquinone derivative. A method of treating lung cancer can include administering to a patient in need thereof a therapeutically effective amount of the naphthoquinone derivative or a pharmaceutical composition including the naphthoquinone derivative.

The naphthoquinone derivative or compositions thereof can be administered to a patient by any suitable route for treating lung cancer or microbial infections. Parenteral, otic, ophthalmic, nasal, inhalable, buccal, sublingual, enteral, topical, oral, peroral, and injectable dosage forms are particularly useful. Particular dosage forms include a solid or liquid dosage forms. Exemplary suitable dosage forms include tablet, capsule, pill, caplet, troche, sache, solution, suspension, dispersion, vial, bag, bottle, injectable liquid, i.v. (intravenous), i.m. (intramuscular) or i.p. (intraperitoneal) administrable liquid and other such dosage forms known to the artisan of ordinary skill in the pharmaceutical sciences.

The amount of the naphthoquinone derivative incorporated in a dose can be selected according to the examples provided herein and/or according to known principles of pharmacy. An effective amount or therapeutically effective amount is specifically contemplated. By the term "effective amount", it is understood that, with respect to, for example, pharmaceuticals, a pharmaceutically effective amount is contemplated. A pharmaceutically effective amount is the amount or quantity of active ingredient which is enough for the required or desired therapeutic response, or in other words, the amount, which is sufficient to elicit an appreciable biological response when, administered to a patient. The appreciable biological response, e.g., anti-microbial activity, anti-cancer activity, can occur as a result of administration of single or multiple doses of an active substance. A dose may comprise one or more dosage forms. It will be understood that the specific dose level for any patient will depend upon a variety of factors including the indication being treated, severity of the indication, patient health, age, gender, weight, diet, pharmacological response, the specific dosage form employed, and other such factors.

The present teachings will be understood more readily by reference to the following examples, which are provided by way of illustration.

Example 1

Isolation of *Streptomyces* sp. ERINLG-201

FIG. 1 shows a flow chart for the isolation of a novel naphthoquinone derived cyclic amide from *Streptomyces* sp. (ERINLG-201). The *Streptomyces* sp. isolate ERINLG-201 was recovered from Kodanad forest, (Southern Western Ghats) Tamil Nadu, India. The strain was Gram-positive filamentous bacterium. The culture characteristics of the new isolate were observed after 7, 14 and 21 days of incubation on different media. The color of the substrate mycelia was white. ERINLG-201 (*Streptomyces* sp.) showed good growth on medium amended with sodium chloride up to 9%; no growth was seen at 12%. The temperature for growth ranged from 25 to 37° C. with optimum of 30° C. and the pH range was 6-12 with normal pH of 7. Utilization of various carbon sources by ERINLG-201 indicated a wide pattern of carbon source assimilation. Arabinose, mannitol and rhamnose did not support the growth of the isolate. ERINLG-201 showed sensitivity towards ciprofloxacin, gentamicin, ampicillin, cephaloridine, erythromycin, vencomycin, amikacin, penicillin, rifamycin and norfloxacin. Gram staining, morphology and cultural characteristics of *Streptomyces* sp. isolate ERINLG-201 indicated that it was Gram positive, aerobic and grew well in all media. The partial 16S rRNA gene sequences of isolate ERINLG-201 have been deposited in the GenBank database under accession number KC820651.

The culture inoculate of the isolate *Streptomyces* sp. ERINLG-201 was taken in 500 mL Erlenmeyer flasks containing 150 mL of fermentation medium (*Micromonospora* medium-Glucose-10 g, Starch-24 g, Peptone-3.0 g, Meat extract-3.0 g, Yeast extract-5.0 g, $CaCO_3$-4.0 g, pH-7 and $H_2O$-1 L) and incubated at 30° C. in a shaker (200 rpm) for 12 days. After the $12^{th}$ day, the culture broth was centrifuged at 8000 g for 20 min to remove the biomass. Equal volume of ethyl acetate (1:1 v/v) was added and shaken in a separating funnel. The ethyl acetate layer was removed. The process was repeated thrice and the combined ethyl acetate extract was washed with about ⅓ volume of water. The extract was dried over anhydrous sodium sulphate and distilled in a rotary evaporator and the brown residue obtained was finally dried in vacuum. In detail, 20 L of *Streptomyces* sp. (ERINLG-201) extract was soaked in 10 lit of ethyl acetate for a period of 48 hours. The extract was concentrated at 40° C. using a vacuum rotary evaporator.

The crude ethyl acetate extract was adsorbed on to silica gel (15 g, 60-120 mesh) and subjected to silica gel column chromatography (Acme's 200 g, 100-200 mesh). The column was successively eluted with hexane, hexane:ethyl acetate, ethyl acetate and ethyl acetate:methanol gradients. Based on thin layer chromatography (TLC) profiles, the fractions were combined to give 15 fractions. Eluted fractions were evaluated by TLC and combined to give 15 major fractions. Table 1 shows the fractions. Surprisingly, the active compound was found only in fraction 12.

TABLE 1

| Fraction-1 | Hexane (100%) |
| --- | --- |
| Fraction-2 | Hexane: Ethyl acetate (90:10) |
| Fraction-3 | Hexane: Ethyl acetate (80:20) |
| Fraction-4 | Hexane: Ethyl acetate (70:30) |
| Fraction-5 | Hexane: Ethyl acetate (60:40) |
| Fraction-6 | Hexane: Ethyl acetate (50:50) |
| Fraction-7 | Hexane: Ethyl acetate (30:70) |
| Fraction-8 | Hexane: Ethyl acetate (20:80) |
| Fraction-9 | Ethyl acetate (100%) |
| Fraction-10 | Ethyl acetate: Methanol (90:10) |
| Fraction-11 | Ethyl acetate: Methanol (80:20) |
| Fraction-12 | Ethyl acetate: Methanol (70:30) |
| Fraction-13 | Ethyl acetate: Methanol (60:40) |
| Fraction-14 | Ethyl acetate: Methanol (50:50) |
| Fraction-15 | Methanol (100%) |

Figure 2:
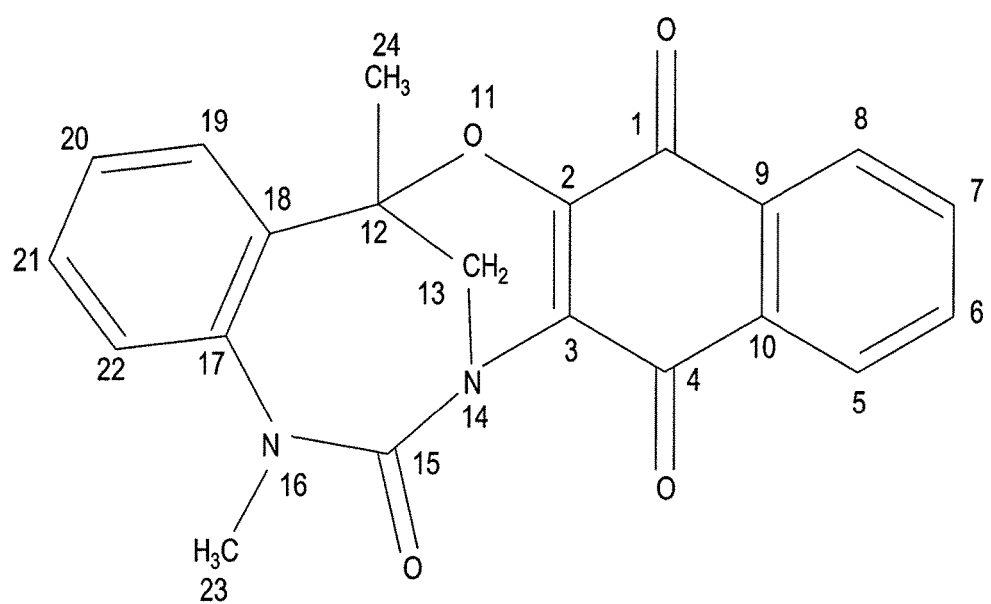
FIG. 2 shows the representative structure of the naphthoquinone derivative.
Figure 3:
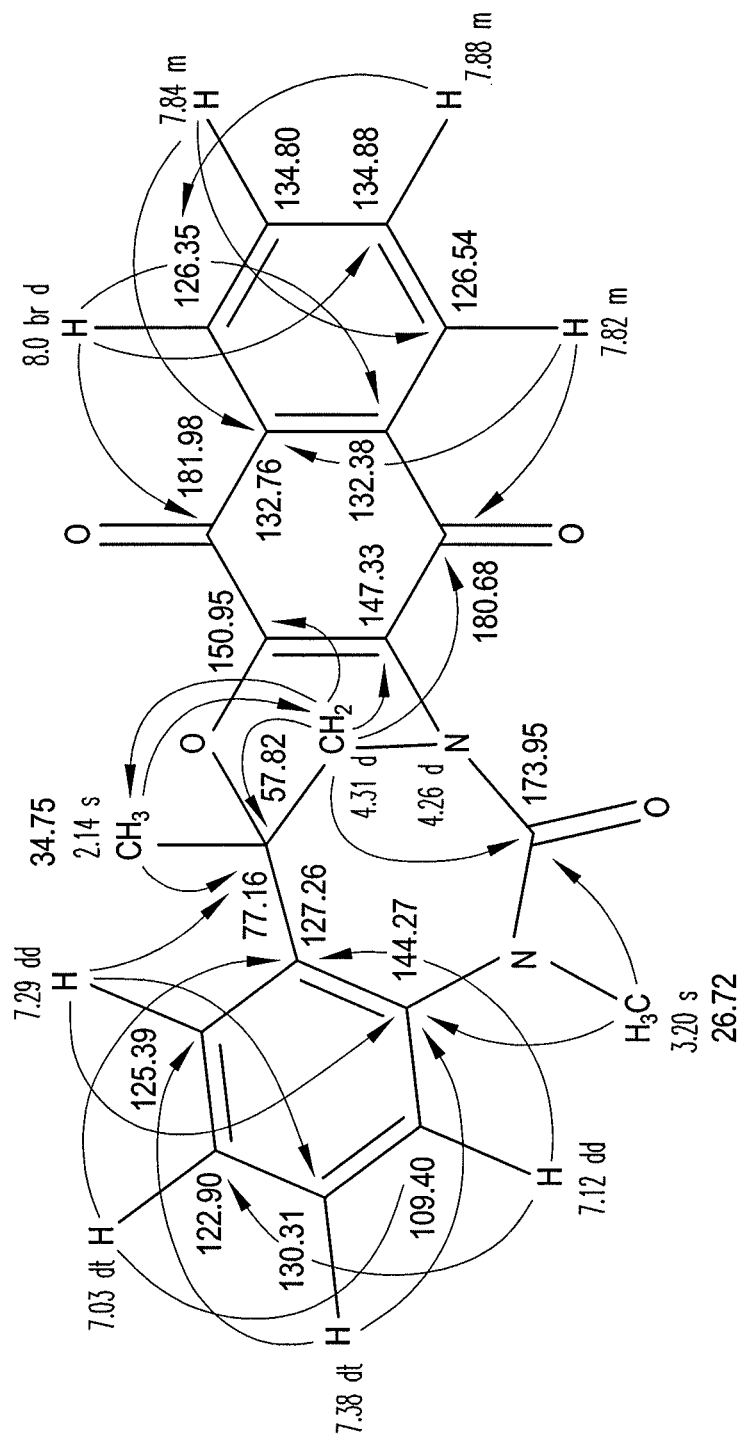
FIG. 3 represents the correlation of the $^1$H and $^{13}$C-NMR signals with the carbon and the protons of the naphthoquinone derivative shown in FIG. 2.
Figure 4:
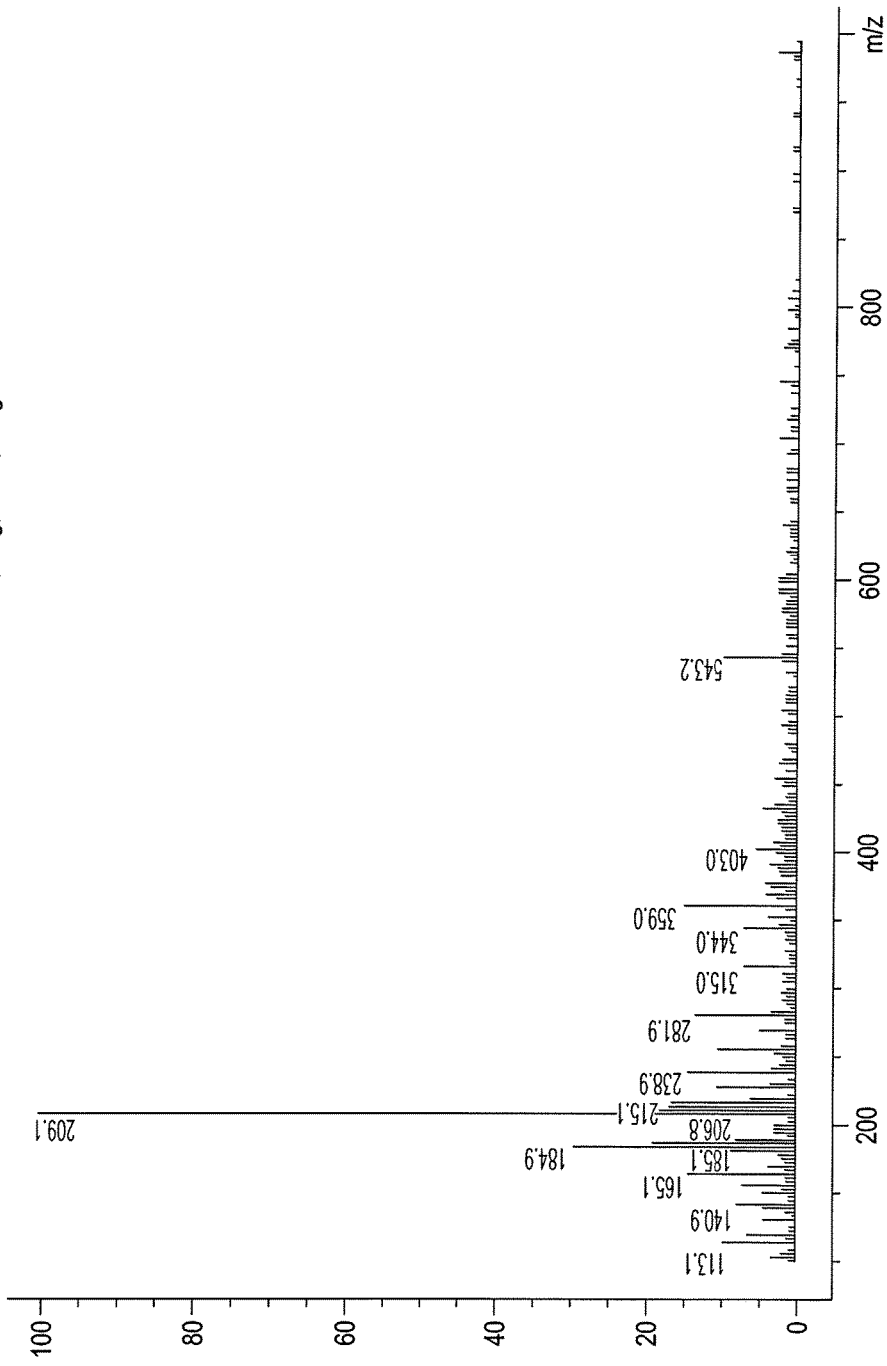
FIG. 4 shows the mass spectrum of the naphthoquinone derivative obtained in a negative mode.
Figure 5:
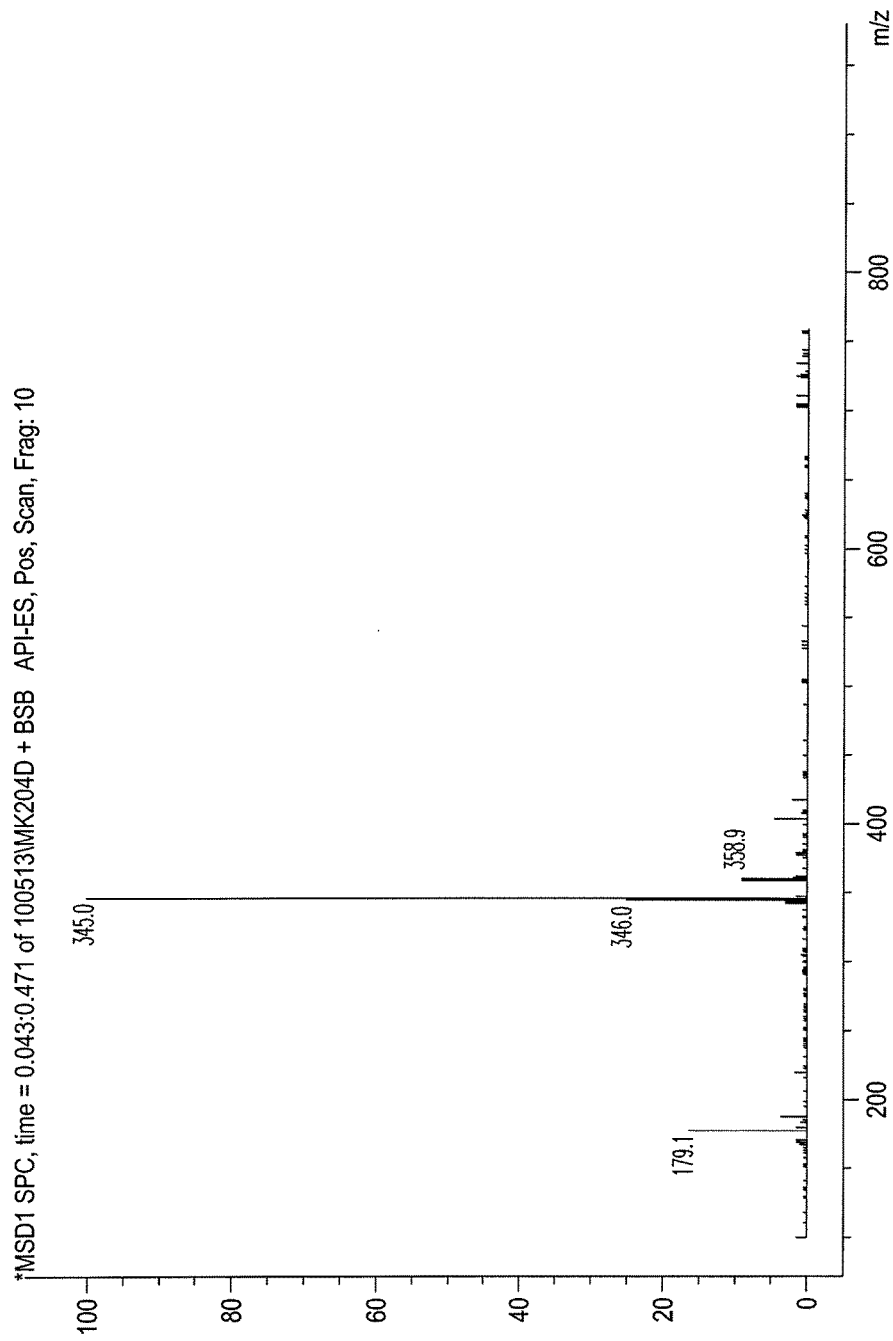
FIG. 5 shows the mass spectrum of the naphthoquinone derivative obtained in a positive mode.

The purified and isolated compound was named "Bluemomycin", which was obtained as a reddish orange amorphous powder from methanol ether mixer (Yield-130 mg). FIG. 2 illustrates the structural representation of Bluemomycin. FIG. 3 represents the correlation of the $^1H$ and $^{13}C$ NMR signals with the carbon and the protons of the Bluemomycin. The purity of the isolated compound was analyzed using High-Performance Liquid Chromatography (HPLC). The compound gave a single spot on TLC over silica gel with ethyl acetate:methanol (1:2) as the developing system (Rf-0.45). The exemplary mass spectrum of the Bluemomycin compound is provided in FIGS. 4 and 5. It was analysed for $C_{21}H_{16}N_2O_4$ (API-MS –ve mode m/z 359 $[M-H]^-$, +ve mode m/z 345 $[M+CH3]^+$) (C, 70%, H, 4.44%, N, 7.78%, O, 17.78%. Found C, 70.5%, H, 4.51%, N, 7.81%) (Oxygen, 17.18%). The compound did not answer dragendorff test for alkaloid. It gave positive test for quinine (dark pink color). The compound did not give ferric reaction for phenol.

Figure 6:
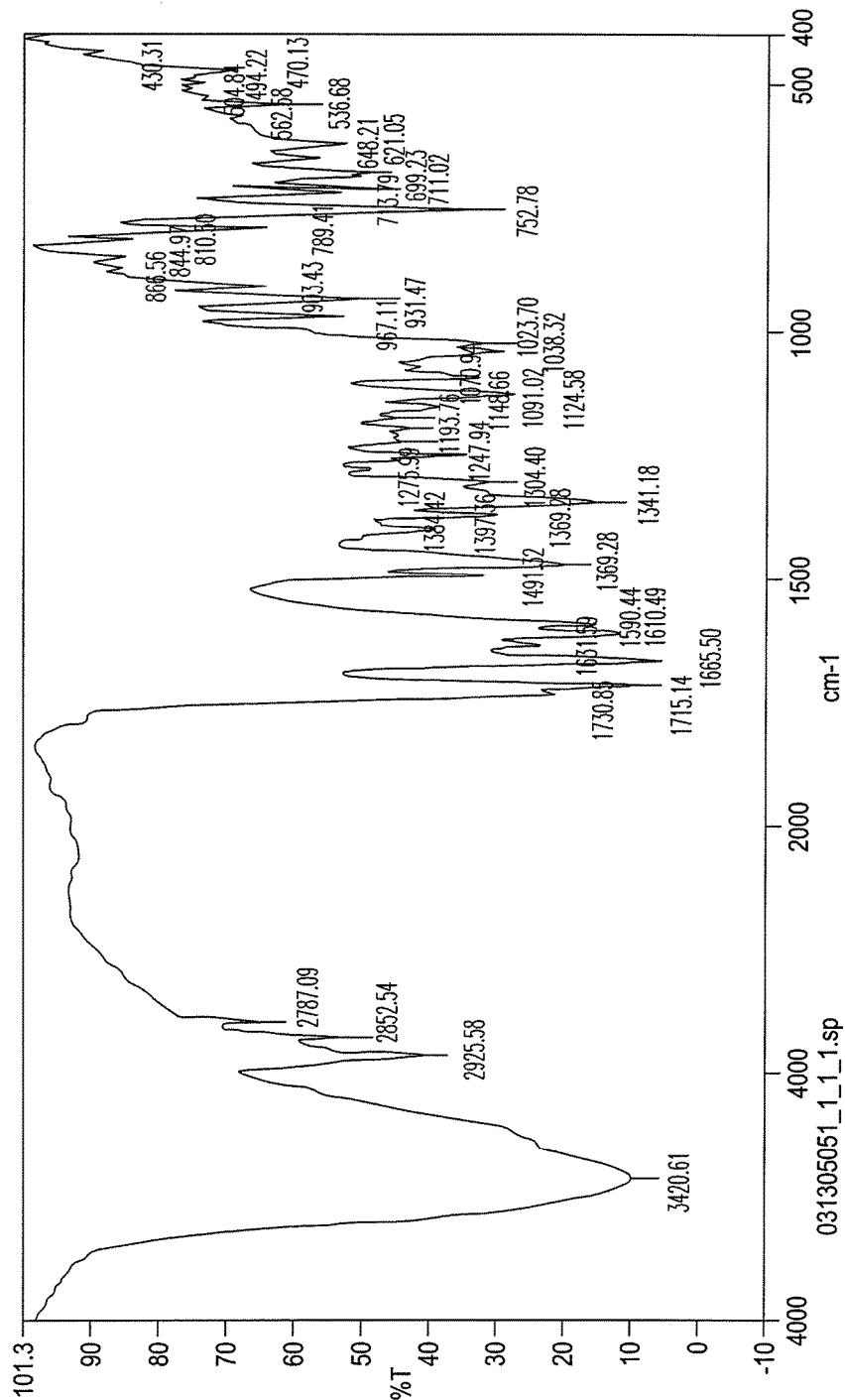
FIG. 6 shows the FT-IR spectrum of the naphthoquinone derivative.
Figure 7:
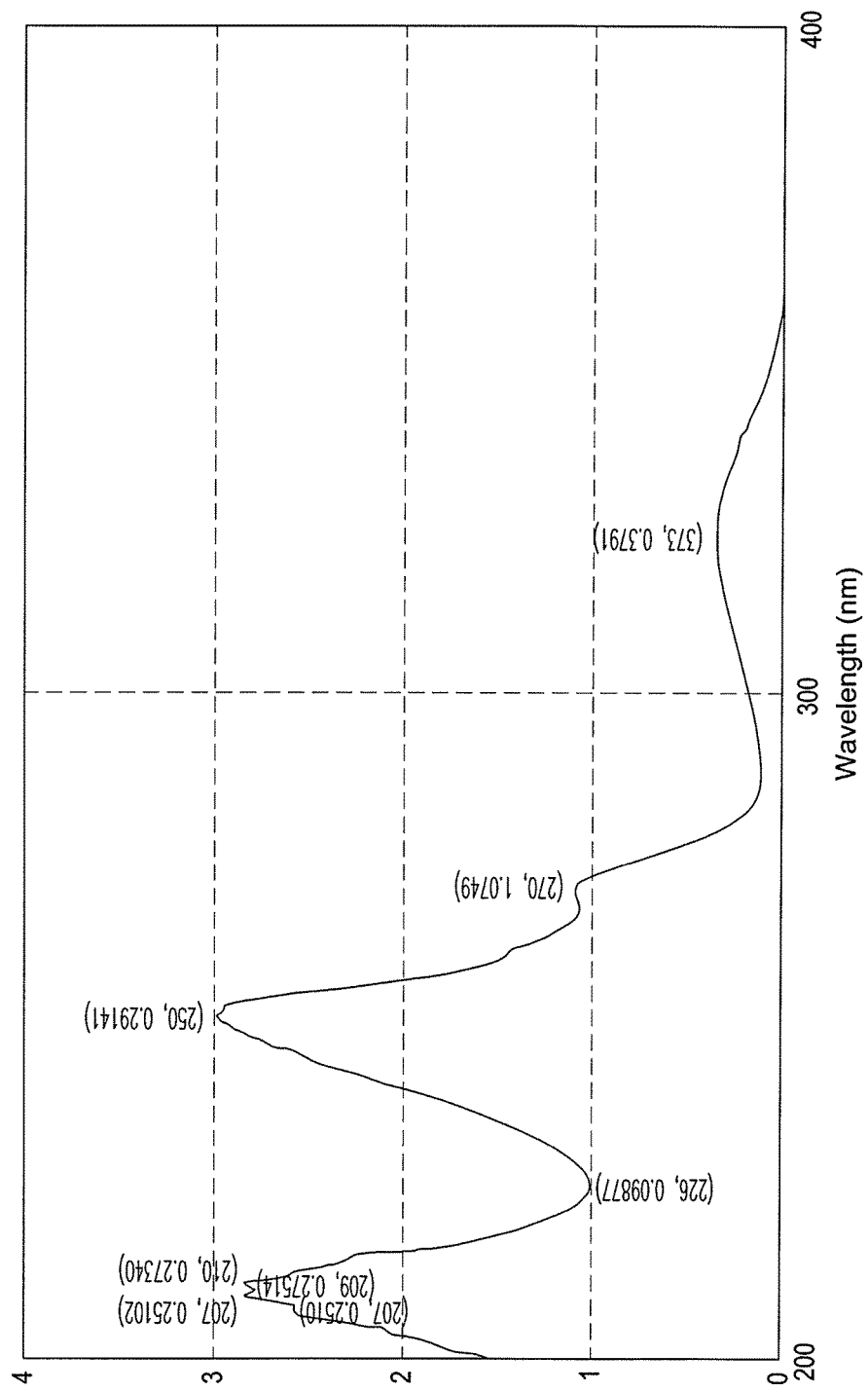
FIG. 7 shows the UV spectrum of the naphthoquinone derivative.
Figure 8:
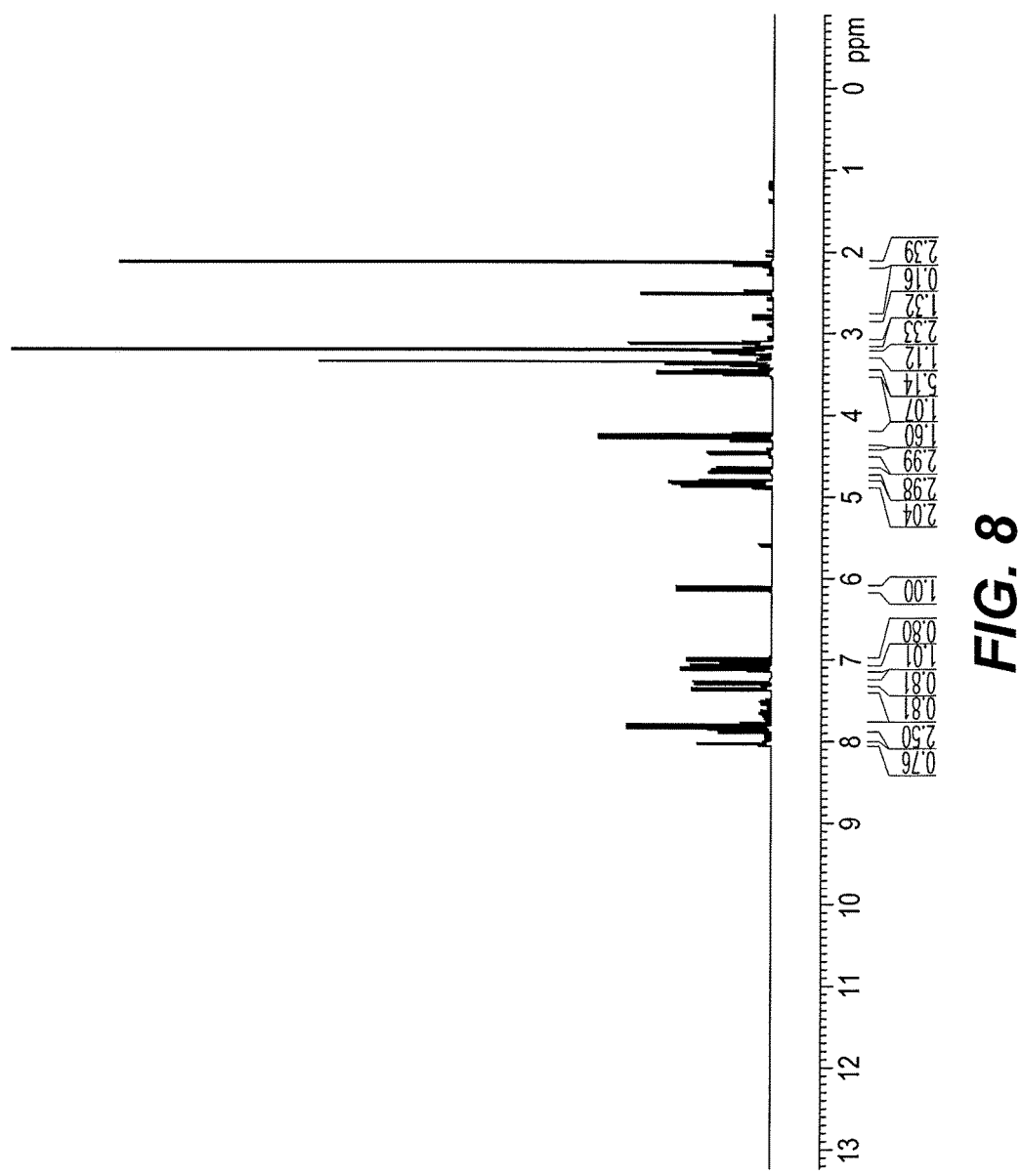
FIG. 8 shows $^1$H-NMR spectrum of the naphthoquinone derivative.
Figure 9:
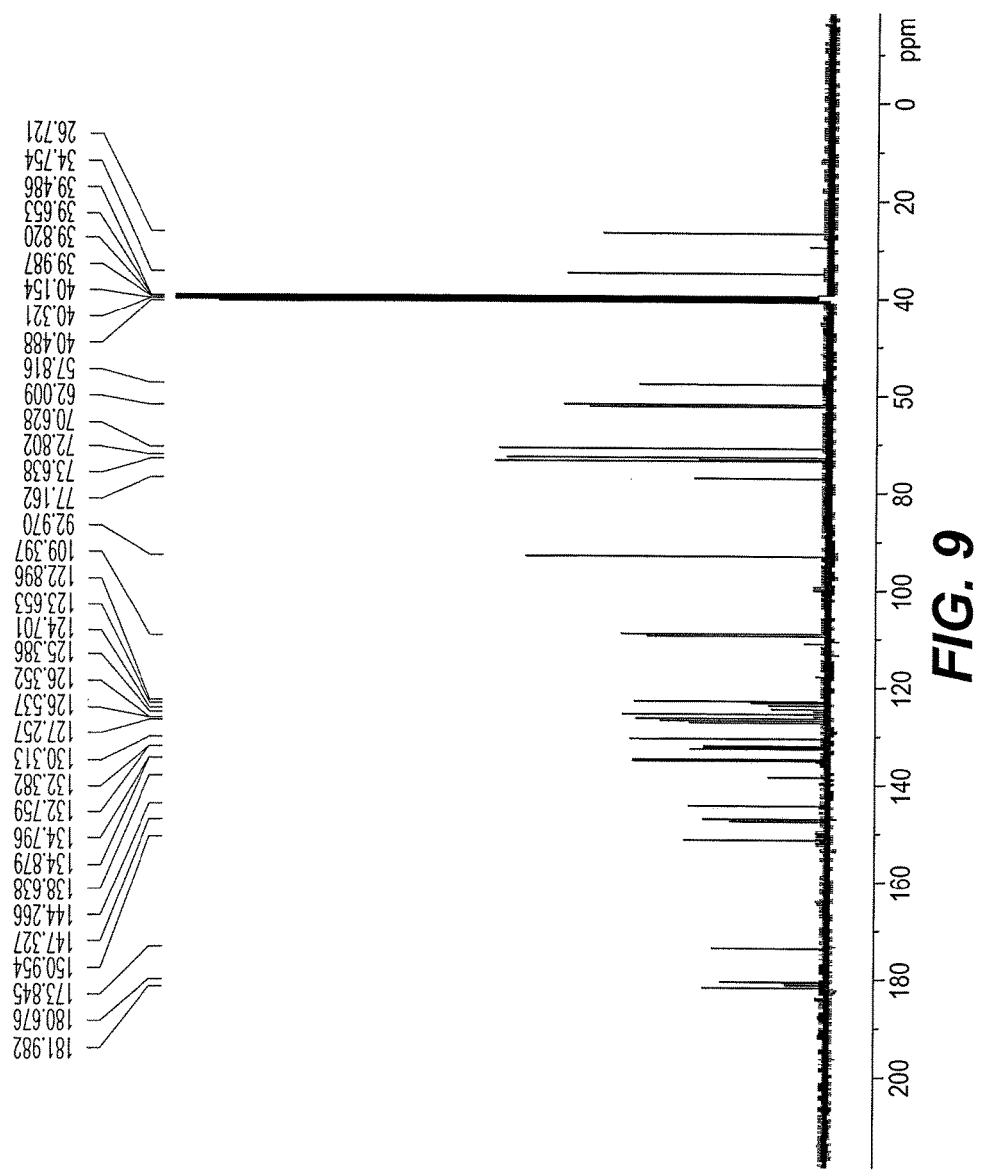
FIG. 9 shows the $^{13}$C-NMR spectrum of the naphthoquinone derivative.
Figure 10:
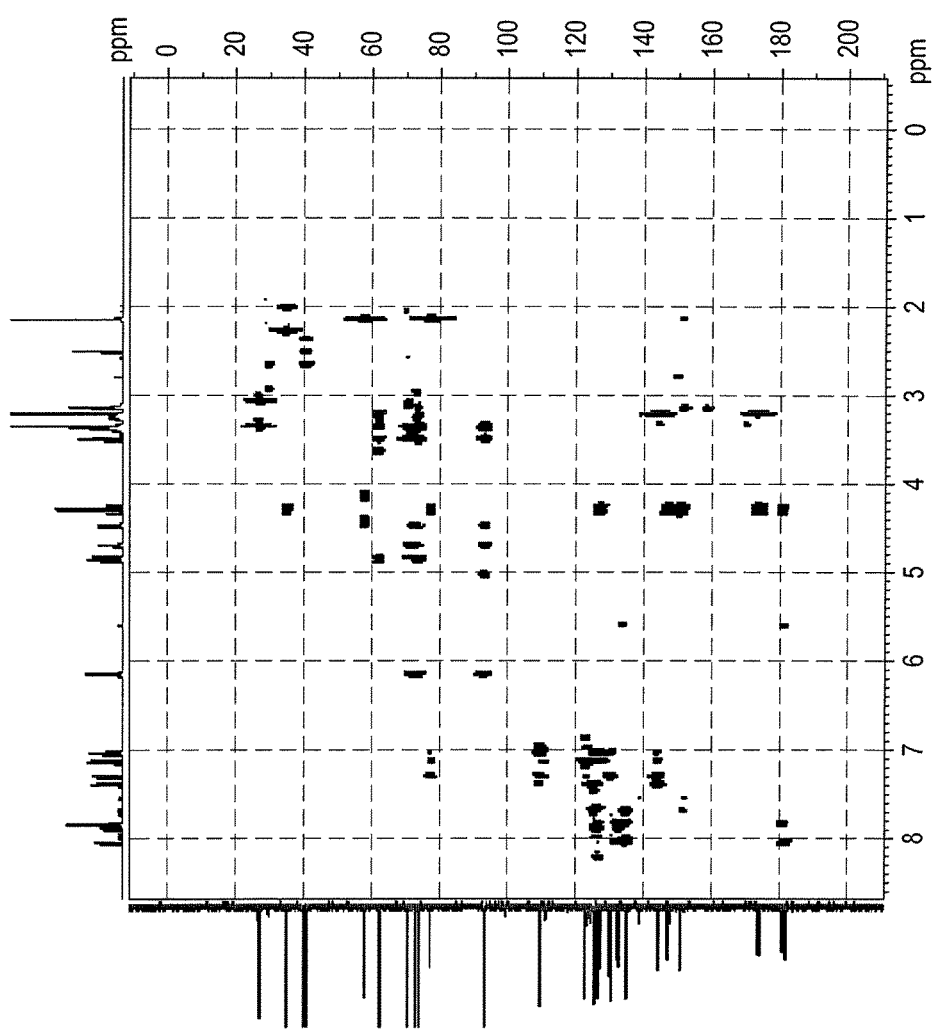
FIG. 10 shows the Heteronuclear Multiple Bond Correlation (HMBC) spectrum of the naphthoquinone derivative.
Figure 11:
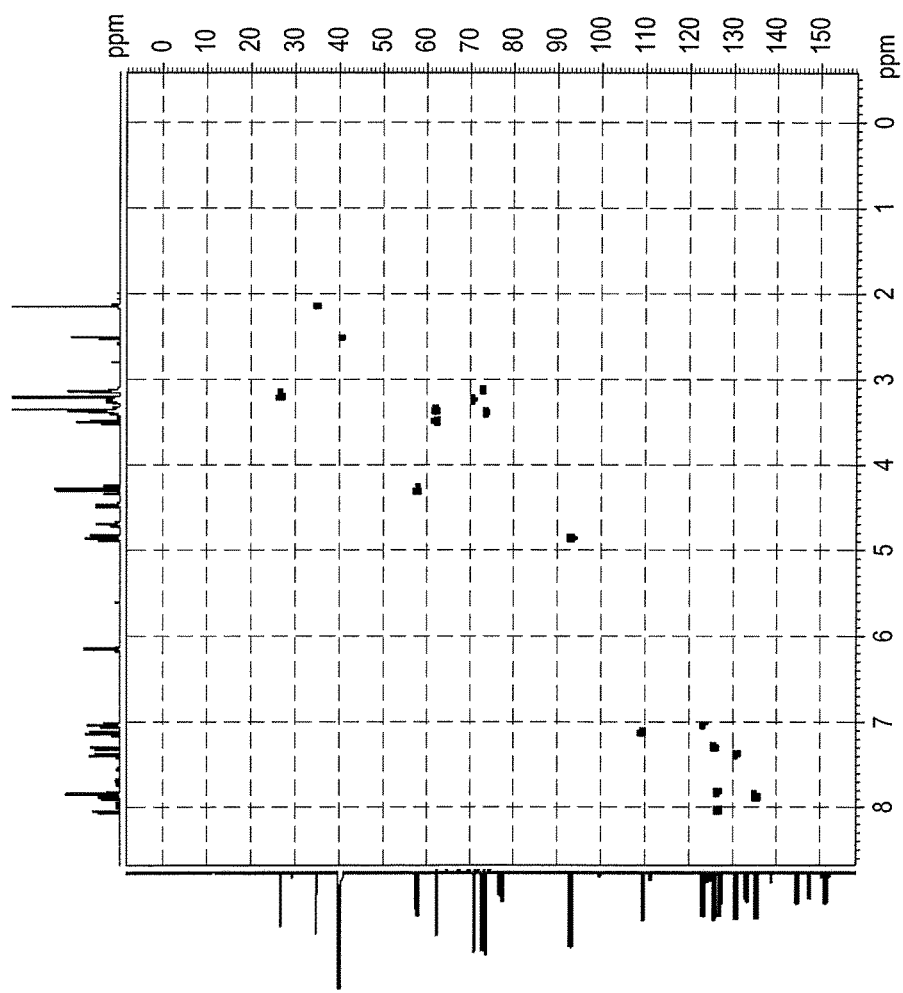
FIG. 11 shows the Heteronuclear Single Quantum Coherence (HSQC) spectrum of the naphthoquinone derivative Similar reference characters denote corresponding features consistently throughout the attached drawings.

The exemplary FT-IR spectrum of the isolated and purified Bluemomycin compound is shown in FIG. 6. It showed peaks for quinone carbonyl (1715 $cm^{-1}$), amide carbonyl (1731 $cm^{-1}$) and aromatic system (1665, 1632, 1611, 1590, 968, 931, 903, 752, 711 $cm^{-1}$). The FT-IR spectrum did not show peaks for hydroxyl group. The exemplary UV spectrum is provided in FIG. 7. The UV spectrum showed maxima at 225, 270 and 323 nm suggesting a naphthoquinone derived cyclic amide. The exemplary $^1H$-NMR spectrum is shown in FIG. 8. The $^1H$-NMR spectrum showed eight aromatic hydrogens one NME, CME and $CH_2$ having no adjacent hydrogens. The $^{13}C$-NMR spectrum as illustrated in FIG. 9 showed one NME, CME, $CH_2$, eight CH, two quinone C=O, one amide C=O and one tertiary carbon attached to oxygen atom. Based on the above data and also on 2D NMR studies reported ($H^1$—$H^1$ COSY, HSQC, and HMBC) (FIGS. 10 and 11), the compound Bluemomycin was found to be a naphthoquinone derived cyclic amide with a seven membered ring containing an amide function. This is a novel compound isolated from *Streptomyces* sp. (ERINLG-201) with a new skeleton so far not reported.

Table 2 shows the $^1H$ and $^{13}C$ NMR assignment of the purified and isolated new compound Bluemomycin with HMBC correlation.

TABLE 2

| Carbon No. | δ Carbon | δ Hydrogen | HMBC |
| --- | --- | --- | --- |
| C-1 | 181.98 | | |
| C-2 | 150.95 | | |
| C-3 | 147.33 | | |
| C-4 | 180.68 | | |
| C-5 | 126.54 | 7.28 (m) | C-4, C-9 |
| C-6 | 134.88 | 7.88 (m) | C-8 |
| C-7 | 134.80 | 7.84 (m) | C-5, C-9 |
| C-8 | 126.35 | 8.00 (dd, 7.5, 1.0) | C-1, C-6, C-10 |
| C-9 | 132.76 | | |
| C-10 | 132.38 | | |
| C-12 | 77.16 | | |
| C-13 | 57.82 | 4.26 and 4.31 (each d, 17.0) | C-2, C-3, C-4, C-12, C-15, C-18, C-24 |
| C-15 | 173.95 | | |
| C-17 | 144.27 | | |
| C-18 | 127.26 | | |
| C-19 | 125.39 | 7.29 (dd, 7.5, 1.0) | C-12, C-17, C-22 |
| C-20 | 122.90 | 7.03 (dt, 7.5, 1.0) | C-18, C-22 |
| C-21 | 130.31 | 7.38 (dt, 7.5, 1.5) | C-17, C-19 |
| C-22 | 109.40 | 7.12 (dd, 7.6) | C-18, C-20 |
| C-23 | 26.72 | 3.20 (s) | C-15, C-17 |
| C-24 | 34.75 | 2.14 (s) | C-12, C-13 |

Example 3

Antimicrobial Activity

Minimum inhibitory concentration (MIC) studies of the isolated compound were performed according to the standard reference methods for bacteria, for filamentous fungi (CLSI 2008) and yeasts NCCLS/CLSI 2002). The required concentrations (100, 75, 50, 25, 12.5, 6.25 and 3.125 µg/mL) of the compound were dissolved in DMSO (2%), and diluted to give serial two-fold dilutions that were added to each medium in 96 well plates. An inoculum of 100 µL from each well was inoculated. The antifungal agent Ketoconazole and antibacterial agent Streptomycin were included in the assays as positive controls. For fungi, the plates were incubated for 48 to 72 hours at 28° C. and for bacteria the plates were incubated for 24 h at 37° C. The Minimum Inhibitory Concentration (MIC) for fungi was defined as the lowest extract concentration, showing no visible fungal growth after incubation time. 5 µL of tested broth was placed on the sterile MHA plates for bacteria and incubated at respective temperature. The MIC for bacteria was determined as the lowest concentration of the compound inhibiting the visual growth of the test cultures on the agar plate. Table 3 shows the Minimum Inhibitory Concentration (MIC) of Bluemomycin against tested bacteria and fungi.

TABLE 3

| Organism | C-5 | Streptomycin |
|---|---|---|
| Gram positive Bacteria | | |
| Bacillus subtilis | 50 | 25 |
| Micrococcus luteus | 25 | 6.25 |
| Staphylococcus aureus | >100 | 6.25 |
| Staphylococcus epidermidis | 50 | 25 |
| Gram negative Bacteria | | |
| Enterobacter aerogenes | 12.5 | 25 |
| Klebsiella pneumoniae | 6.25 | 25 |
| Proteus vulgaris | 100 | 6.25 |
| Pseudomonas aeruginosa | 12.5 | 25 |
| Salmonella paratyphi-B | 25 | 6.25 |
| Salmonella typhimurium | 12.5 | 25 |
| Shigella flexneri | 12.5 | 6.25 |
| Clinical isolates | | |
| Staphylococcus aureus (MRSA) | 25 | 6.25 |
| Klebsiella pneumoniae (ESBL-3894) | 12.5 | 6.25 |
| Kiebsiella pneumoniae (ESBL-75799) | 12.5 | 25 |
| Klebsiella pneumoniae (ESBL-3967) | 6.25 | 25 |
| Klebsiella pneumoniae (ESBL-3971) | >100 | 6.25 |
| Escherichia coli (ESBL-3904) | 25 | 25 |
| Escherichia coli (ESBL-3984) | 12.5 | 25 |
| Fungi | | Ketoconazole |
| Candida albicans | 50 | 25 |
| Malassezia pachydermatis | 50 | 25 |

Example 5

Cytotoxic Activity

A549 lung adenocarcinoma cancer cell line was obtained from the National Institute of Cell Sciences, Pune. A549 cell line was maintained in complete tissue culture medium Dulbecco's Modified Eagle's Medium with 10% Fetal Bovine Serum and 2 mM L-Glutamine, along with antibiotics (about 100 International Unit/mL of penicillin, 100 µg/mL of streptomycin) with the pH adjusted to 7.2. The cytotoxicity was determined according to the method of Balachandran et al., (2013) with some changes. Cells (5000 cells/well) were seeded in 96 well plates containing medium with different concentrations such as 100, 80, 60, 40, 20, and 10 µg/mL. The cells were cultivated at 37° C. with 5% $CO_2$ and 95% air in 100% relative humidity. After various durations of cultivation, the solution in the medium was removed. An aliquot of 100 µL of medium containing 1 mg/mL of 3-(4,5-dimethylthiazol-2-yl)-2,5-diphenyl-tetrazolium bromide was loaded in the plate. The cells were cultured for 4 h and then the solution in the medium was removed. An aliquot of 100 µL of DMSO was added to the plate, which was shaken until the crystals were dissolved. The cytotoxicity against cancer cells was determined by measuring the absorbance of the converted dye at 540 nm in an Enzyme linked immune sorbant assay (ELISA) reader. Cytotoxicity of each sample was expressed as the half maximal inhibitory concentration ($IC_{50}$) value. The $IC_{50}$ value is the concentration of test sample that causes 50% inhibition of cell growth, averaged from three replicate experiments. Table 4 shows the cytotoxic properties of Bluemomycin.

TABLE 4

| Concentration (µg/mL) | % | Compound Mean ± S.D |
|---|---|---|
| 5 | 10.5 | 0.565 ± 0.00384 |
| 10 | 26.3 | 0.465 ± 0.00376 |
| 20 | 51.7 | 0.305 ± 0.00346 |
| 40 | 60.2 | 0.251 ± 0.00622 |
| 60 | 68.6 | 0.198 ± 0.00353 |
| 80 | 78.6 | 0.135 ± 0.00376 |
| 100 | 88.7 | 0.071 ± 0.00203 |

Data are mean ± SD of three independent experiments with each experiment conducted in triplicate. Positive control 9.80 ± 0.43 µm (Cisplatin).

It should be readily understood to those skilled in the art that several advantages naturally flows from this invention. For example, the naphthoquinone derivative, i.e., ethyl acetate extract of *Streptomyces* sp. (ERINLG-201) exhibits significant antimicrobial activity against many bacteria, fungi and A549 human lung cancer cell line. The naphthoquinone derivative is found to be responsible for antimicrobial and cytotoxic activities, which is confirmed by spectroscopic data. Naphthoquinone derived cyclic amide enhances the antimicrobial and cytotoxic activities.

Since the naphthoquinone derived cyclic amide compound, e.g., Bluemomycin, possesses antimicrobial activity against tested bacteria and fungi, it would therefore be useful for controlling other microbes like viruses and drug resistant organisms. In addition, this compound has cytotoxic activity against A549 human lung cancer cell line. The isolated compound is not harmful to humans. The compound of the present invention can also be used for other medical and pharmaceutical applications.

It is to be understood that the present invention is not limited to the embodiments described above, but encompasses any and all embodiments within the scope of the following claims.

We claim:
1. A process for obtaining a naphthoquinone derivative from *Streptomyces* sp., comprising the steps of:
   providing a seed inoculum of *Streptomyces* sp.;
   culturing the *Streptomyces* sp. in a culture nutrient medium;

centrifuging the culture nutrient medium to provide a supernatant and a biomass precipitate;

admixing a water immiscible solvent to the supernatant in a ratio of 1:1 to produce a water immiscible solvent extract layer and a water layer; and isolating the naphthoquinone derivative from the water immiscible solvent extract layer, wherein the naphthoquinone derivative has the following structural formula:

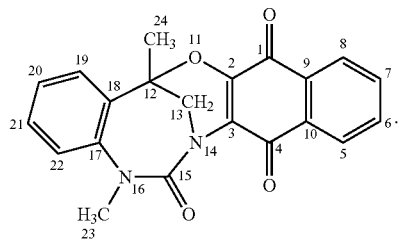 [SMILES: CN1C(=O)N2CC(C)(OC3=C2C(=O)c2ccccc2C3=O)c2ccccc21]

2. The process according to claim 1, wherein the water immiscible solvent is ethyl acetate.

3. The process according to claim 1, wherein the step of admixing a water immiscible solvent to the supernatant is repeated at least two times to produce a water immiscible solvent extract.

4. The process according to claim 1, wherein the isolating the naphthoquinone derivative from the water immiscible solvent extract further comprises:

drying the water immiscible solvent extract over anhydrous sodium sulphate;

concentrating the water immiscible solvent fraction by evaporation to produce a concentrated volume of the water immiscible solvent fraction; and isolating the purified naphthoquinone derivative by performing silica gel chromatography of the concentrated volume of the water immiscible solvent fraction.

5. The process according to claim 4, wherein the performing silica gel chromatography comprises:

loading the concentrated volume of the water immiscible solvent fraction on a silica gel column;

eluting the silica gel column with a fractionating solvent mixture;

collecting solvent fractions at various time intervals; and isolating the naphthoquinone derivative from at least one of the solvent fractions by evaporating off the solvent.

6. The process according to claim 5, wherein the solvent fraction includes an ethyl acetate:methanol ratio of 70:30.

7. The process according to claim 5, wherein the fractionating solvent is selected from the group consisting of hexane, ethyl acetate, methanol, and combinations thereof.

8. A naphthoquinone derivative isolated from an extract of *Streptomyces*, the naphthoquinone derivative having the following structural formula:

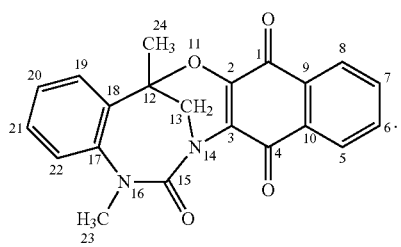

9. A method of treating microbial infections, comprising administering to a patient in need thereof a therapeutically effective amount of the naphthoquinone derivative of claim 8.

10. The method of treating microbial infections according to claim 9, wherein the microbial infections are caused by gram positive bacteria, gram negative bacteria, or fungi.

11. A method of treating lung cancer, comprising administering to a patient in need thereof a therapeutically effective amount of the naphthoquinone derivative of claim 8.

* * * * *